United States Patent [19]

Deusser et al.

[11] Patent Number: 5,429,873
[45] Date of Patent: Jul. 4, 1995

[54] SURFACE-MODIFIED SILICON DIOXIDES

[75] Inventors: Hans Deusser, Karlstein; Thomas Göbel, Hanau; Jürgen Meyer, Stockstadt; Michael Günther, Karlstein; Andreas Stübbe, Rodenbach, all of Germany

[73] Assignee: Degussa Aktiengesellschaft, Frankfurt am Main, Germany

[21] Appl. No.: 957,362

[22] Filed: Oct. 7, 1992

Related U.S. Application Data

[62] Division of Ser. No. 713,076, Jun. 11, 1991, abandoned.

[30] Foreign Application Priority Data

Jul. 19, 1990 [EP] European Pat. Off. ........... 93113839

[51] Int. Cl.⁶ ................................. B32B 5/16
[52] U.S. Cl. ................ 428/405; 106/287.13; 106/287.16; 106/287.27
[58] Field of Search ................ 428/405, 331; 427/387, 427/452; 106/484, 285, 287.13, 287.16, 287.27, 287.34, 490

[56] References Cited

U.S. PATENT DOCUMENTS

| | | | |
|---|---|---|---|
| 4,208,316 | 6/1980 | Nauroth et al. ................ | 428/405 X |
| 4,877,595 | 10/1989 | Klingle et al. ................ | 423/335 |
| 4,950,634 | 8/1990 | Williams et al. ................ | 502/401 |
| 4,973,540 | 11/1990 | Machida et al. ................ | 430/110 |
| 5,002,918 | 3/1991 | Deller et al. ................ | 502/263 |
| 5,013,585 | 5/1991 | Shimizu et al. ................ | 427/220 |

Primary Examiner—D. S. Nakarani
Assistant Examiner—H. T. Lê
Attorney, Agent, or Firm—Cushman Darby & Cushman

[57] ABSTRACT

Surface-modified, pyrogenically produced silicon dioxide is obtained by placing a pyrogenically produced silicon dioxide in a know mixing device, spraying it with a chemical compound from the group:

$$CHF_2-CF_2-O-(CH_2)_3-Si(OCH_3)_3$$

$$CF_3-CHF-CF_2-O-(CH_2)_3-Si(OCH_3)_3$$

$$C_4F_9-CH_2-CH_2-Si(OCH_3)_3$$

$$C_6F_{13}-CH_2-CH_2-Si(OCH_3)_3$$

with intensive mixing, subsequently mixing it and tempering the mixture obtained for a fairly long time.

1 Claim, No Drawings

SURFACE-MODIFIED SILICON DIOXIDES

This is a division of application Ser. No. 07/713,076, filed Jun. 11, 1991, now abandoned.

The present invention relates to surface-modified, pyrogenically produced silicon dioxides, their production and use in toners,

BACKGROUND OF THE INVENTION

It is known that powdery toners can be used in electrostatic development processes which toners contain surface-modified, pyrogenically produced silicon dioxide. Various silanes, especially dimethyldichlorosilane, are used for surface-modification (see U.S. Pat. No. 3,720,617 and European Patent Application EP-A 0,293,009).

SUMMARY OF THE INVENTION

The present invention relates to a surface-modified, pyrogenically produced silicon dioxide, characterized in that the modification was carried out with the chemical compounds $$CHF_2-CF_2-O-(CH_2)_3Si(OCH_3)_3$$

and that the modified silicon dioxide has the following physico-chemical properties:

| Appearance | loose white powder |
|---|---|
| Surface according to[1] BET | 170 ± 30 |
| Average size of the primary particles nm | 12 |
| Stamping density[2] | 60 ± 20 |
| Drying loss[3] 2 h at 105° C. | <2 |
| Annealing loss[2] [6] | 6.5 ± 2.0 |
| Carbon content | 2.4 ± 0.5 |
| pH[5] (in 4% aqueous dispersion) | 3.5–5.5 |

[1]according to DIN 66 131
[2]according to DIN ISO 787/XI, JIS K 5101/18
[3]according to DIN ISO 787/II, ASTM D 280, JIS K 5101/21
[4]according to DIN 55921, ASTM D 1208, JIS K 5101/23
[5]according to DIN ISO 787/IX, ASTM D 1208, JIS K 5101/24
[6]relative to the substance dried 2 hours at 105° C.

The invention also provides a surface-modified, pyrogenically produced silicon dioxide, characterized in that the modification was carried out with the chemical compound $$CF_3-CHF-CF_2-O-(CH_2)_3-Si(OCH_3)_3$$

and that the modified silicon dioxide has the following physico-chemical properties:

| Appearance | loose white powder |
|---|---|
| Surface according to[1] BET | 170 ± 30 |
| Average size of the primary particles nm | 12 |
| Stamping density[2] | 60 ± 20 |
| Drying loss[3] 2 h at 105° c. | <2 |
| Annealing loss[2] [6] | 7.0 ± 2.0 |
| Carbon content | 2.2 ± 0.5 |
| pH[5] (in 4% aqueous dispersion) | 3.5–5.5 |

[1]according to DIN 66 131
[2]according to DIN ISO 787/XI, JIS K 5101/18
[3]according to DIN ISO 787/II, ASTM D 280, JIS K 5101/21
[4]according to DIN 55921, ASTM D 1208, JIS K 5101/23
[5]according to DIN ISO 787/IX, ASTM D 1208, JIS K 5101/24
[6]relative to the substance dried 2 hours at 105° C.

The invention also provides a surface-modified, pyrogenically produced silicon dioxide, characterized in that the modification was carried out with the chemical compound $$C_4F_9-CH_2-CH_2-Si(OCH_3)_3$$

and that the modified silicon dioxide has the following physico-chemical characteristics:

| Appearance | loose white powder |
|---|---|
| Surface according to[1] BET | 170 ± 30 |
| Average size of the primary particles nm | 12 |
| Stamping density[2] | 60 ± 20 |
| Drying loss[3] 2 h at 105° C. | <2 |
| Annealing loss[2] [6] | 7.5 ± 2.0 |
| Carbon content | 2.2 ± 0.5 |
| pH[5] (in 4% aqueous dispersion) | 3.5–5.5 |

[1]according to DIN 66 131
[2]according to DIN ISO 787/XI, JIS K 5101/18
[3]according to DIN ISO 787/II, ASTM D 280, JIS K 5101/21
[4]according to DIN 55921, ASTM D 1208, JIS K 5101/23
[5]according to DIN ISO 787/IX, ASTM D 1208, JIS K 5101/24
[6]relative to the substance dried 2 hours at 105° C.

The invention also provides a surface-modified, pyrogenically produced silicon dioxide, characterized in that the modification was carried out with the chemical compound $$C_6F_{13}-CH_2-CH_2-Si(OCH_3)_3$$

and that the modified silicon dioxide has the following physico-chemical properties:

| Appearance | loose white powder |
|---|---|
| Surface according to[1] BET | 170 ± 30 |
| Average size of the primary particles nm | 12 |
| Stamping density[2] | 60 ± 20 |
| Drying loss[3] 2 h at 105° C. | <2 |
| Annealing loss[2] [6] | 8.5 ± 2 |
| Carbon content | 2.0 ± 0.5 |
| pH[5] (in 4% aqueous dispersion) | 3.5–5.5 |

[1]according to DIN 66 131
[2]according to DIN ISO 787/XI, JIS K 5101/18
[3]according to DIN ISO 787/II, ASTM D 280, JIS K 5101/21
[4]according to DIN 55921, ASTM D 1208, JIS K 5101/23
[5]according to DIN ISO 787/IX, ASTM D 1208, JIS K 5101/24
[6]relative to the substance dried 2 hours at 105° C.

The invention further provides a method of producing surface-modified, pyrogenically produced silicon dioxides, characterized in that a pyrogenically produced silica which has the following physico-chemical properties:

| Surface according to BET | m²/g | 200 ± 25 |
|---|---|---|
| Average size of the primary particles | nanometer | 12 |
| Stamping density[1)] | g/l | approx. 50 |
| Drying loss[2)] (2 h at 105° C. | % | <1.5 |
| Annealing loss[2)][7)] (2 h at 1000° C.) | % | <1 |
| pH[3] (in 4% aqueous dispersion) | | 3.6–4.3 |
| $SiO_2$[5)] | % | >99.8 |
| $Al_2O_3$[5)] | % | <0.05 |
| $Fe_2O_3$[5)] | % | <0.003 |
| $TiO_2$[5)] | % | <0.03 |
| HCl[5)][6)] | % | <0.025 |
| Sieve residue[4)] | % | <0.05 |

[1] according to DIN 53 194
[2] according to DIN 55 921
[3] according to DIN 53 200
[4] according to Din 53 580
[5] relative to the substance annealed 2 hours at 1000° C.
[6] HCl content is a component of the annealing loss
[7] relative to the substance dried 2 hours at 105° C.

is placed in a known mixing device, sprayed with a chemical compound from the group of the silanes

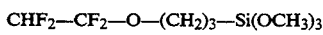

$CHF_2-CF_2-O-(CH_2)_3-Si(OCH_3)_3$ $CF_3-CHF-CF_2-O-(CH_2)_3-Si(OCH_3)_3$ $C_4F_9-CH_2-CH_2-Si(OCH_3)_3$ $C_6F_{13}-CH_2-CH_2-Si(OCH_3)_3$ with intensive mixing, subsequently mixed and the mixture obtained is tempered for a period of 1.5 to 2.5 hours at a temperature of 100° to 140° C.

The pyrogenically produced silica Aerosil 200 is described in:

Ullmanns Enzyklopädie der technischen Chemie, 4th ed. (1982), pp. 464–469 and table 12.

The silanes:

$CHF_2-CF_2-O-(CH_2)_3-Si(OCH_3)_3$ $CF_3-CHF-CF_2-O-(CH_2)_3-Si(OCH_3)_3$ $C_4F_9-CH_2-CH_2-Si(OCH_3)_3$ $C_6F_{13}-CH_2-CH_2-Si(OCH_3)_3$ are produced by reacting trichlorosilane with each of the compounds from the group:

$C_4F_9-CH=CH_2$ $C_6F_{13}-CH=CH_2$ $C_2F_4H-O-CH_2-CH=CH_2$ $C_3F_6H-O\ CH_2=CH_2$

The olefin is placed in iso-propanol solution in the presence of $H_2PtCl_6$ and heated to reflux temperature. The trichlorosilane is added gradually to the solution, during which time the reflux temperature rises from 40° C. to 90°-95° C.

The esterification with methanol or sodium methylate is concluded after two hours at temperatures of 65° to 75° C. The workup takes place according to known methods.

The method described above is partially known from published German patent applications DE-OS 31 38 235 and DE-OS 25 11 187.

The invention also comprises chemical compounds of the formula:

$C_4F_9-CH_2-CH_2-Si(OCH_3)_3$ and of the formula:

$C_6F_{13}-CH_2-CH_2-Si(OCH_3)_3$.

The surface-modified, pyrogenically produced silicas of the invention have the following advantages:
First, the charge stabilities during the use of the toners in an electrostatic development process are better, and, secondly, the activation energies are less.

DETAILED DESCRIPTION OF PREFERRED EMBODIMENTS

Example

The pyrogenically produced silica Aerosil 200 used in the following the following physico-chemical properties:

| | | |
|---|---|---|
| Surface according to BET | m²/g | 200 ± 25 |
| Average size of the primary particles | nanometer | 12 |
| Stamping density[1] | g/l | approx. 50 |
| Drying loss[2] (2 h at 105° C.) | % | <1.5 |
| Annealing loss[2] [7] (2 h at 1000° C.) | % | <1 |
| pH[3] (in 4% aqueous dispersion) | | 3.6–4.3 |
| $SiO_2$[5] | % | >99.8 |
| $Al_2O_3$[5] | % | <0.05 |
| $Fe_2O_3$[5] | % | <0.003 |
| $TiO_2$[5] | % | <0.03 |
| HCl[5][6] | % | <0.025 |
| Sieve residue[4] according to Mocker (45/m) | % | <0.05 |

[1] according to DIN 53 194
[2] according to DIN 55 921
[3] according to DIN 53 200
[4] according to DIN 53 580
[5] relative to the substance annealed 2 hours at 1000° C.
[6] HCl content is a component of the annealing loss
[7] relative to the substance dried 2 hours at 105° C.

The following compounds are used as silanes:

$CHF_2-CF_2-O-(CH_2)_3-Si(OCH_3)_3$   1.

$CF_3-CHF-CF_2-O-(CH_2)_3-Si(OCH_3)_3$   2.

$C_4F_9-CH_2-CH_2-Si(OCH_3)_3$   3.

$C_6F_{13}-CH_2-CH_2-Si(OCH_3)_3$   4.

2 kg Aerosil 200 are placed in a 135 liter Lodige mixer. 200 g silane are sprayed onto the Aerosil with an atomizer nozzle with the mixer running. The mixture is then mixed 15 min. longer. The silanized Aerosil is tempered 2 hours at 120° C.

The surface-modified silicas obtained have the following physico-chemical properties:

| | 1 | 2 | 3 | 4 |
|---|---|---|---|---|
| Appearance | loose white powder | | | |
| Surface according to[1] BET | 175 | 171 | 178 | 174 |
| Average size of the primary particles nm | 12 | 12 | 12 | 12 |
| Stamping density[2] | 58 | 59 | 63 | 61 |
| Drying loss[3] 2 h at 105° C. | 0.3 | 0.45 | 0.70 | 0.83 |
| Annealing loss[2] [6] | 6.67 | 7.04 | 7.46 | 8.62 |
| Carbon content | 2.4 | 2.2 | 2.2 | 2.0 |
| pH[5] (in 4% aqueous dispersion) | 4.76 | 4.56 | 4.77 | 4.67 |

[1] according to DIN 66 131
[2] according to DIN ISO 787/XI, JIS K 5101/18
[3] according to DIN ISO 787/II, ASTM D 280, JIS K 5101/21
[4] according to DIN 55921, ASTM D 1208, JIS K 5101/23
[5] according to DIN ISO 787/IX, ASTM D 1208, JIS K 5101/24
[6] relative to the substance dried 2 hours at 105° C.

TECHNICAL APPLICATION TEST

Influencing the flow behavior of a toner powder by means of the addition of silica The flow behavior was evaluated by measuring the bulk cone height and determination of the running-out behavior.

The raw toner consists of 93% toner resin OT 5201 and 7% pigment black Printex 150 T.

The toner resin OT 5201 has the following technical product properties:

| | | |
|---|---|---|
| Melt flow index[1] (150° C. 2.16 kp) | g/10 min. | 5–10 |
| Viscosity index[2] | cm³/g | 37–43 |
| Weight loss[3] | % by weight | <1 |
| Residual monomers[4] | % by weight | <0.35 |
| Styrene | | <0.25 |
| n-BMA | | <0.10 |
| Monomer composition | | 70% by weight styrene |
| | | 30% by weight n-butylmethacrylate |
| Glass transition | | |
| Temperature Tg[5] | | 60–65° C. |
| Average grain diameter[6] | | (d 50 % RS) 0.200–0.314 mm |

[1]DIN 53 735, edition 2/88
Specimen pretreatment: Drying at 50° C.
Oil pump vacuum, 1 hour or 4 hours
Drying cupboard, 50° C.
[2]DIN 7745, edition 1/80
[3]IR drying device, up to weight constancy
[4]gas chromatography
[5]DSC method, ASTM D 3418/75
[6]DIN 53 734, edition 1/73, evaluation according to DIN 66 141, edition 2/74.

The carbon black Printex 150 T is a commercially available black and exhibits the following physico-chemical properties:

| PRINTEX ® 150 T | | |
|---|---|---|
| Nigrometer index | | 83 |
| Coloring strength DIN 53 204/53 234 (IRB 3 = 100) | | 100 |
| Oil absorption, F.P. | [%] | 400 |
| DPB absorption DIN 53 601 | [ml/100 g] | 115 |
| Annealing loss | [%] | 7 |
| pH DIN 53 200 | | 5 |
| Sieve residue DIN 53 580 | [% max.] | 0.05 |
| Ash content | | 0.05 |
| Stamping density DIN 53 194 | [g/l fluffy] | 150 |
| Average particle size | [nm] | 29 |
| Bet surface | [m²/g] | 110 |

| | Bulk cone (mm) | Running-out behavior (note*) |
|---|---|---|
| Raw toner | 47.6 | 4 |
| Raw toner + silica 1 + 0.3% | 46.5 | 3 |
| Raw toner + silica 2 + 0.3% | 45.4 | 3 |
| Raw toner + silica 3 + 0.3% | 47.5 | 3 |
| Raw toner + silica 4 + 0.3% | 45.0 | 3 |

*publication series "Pigmente", vol. 31, p. 7 q/m measurements

In practice, a toner is subject to very irregular conditions. is constantly reactivated and recharged by turning the copier on and off, after rather long standing times in which no copies are made and during copying. Under these conditions of usage, the charge level (expressed in the q/m value) must be stable. Therefore, the so-called charge retention time and the multiple activation were investigated in order to investigate the properties of test silicas 1, 2, 3 and 4. q/m measuring principle.

The charge/mass ratio (also called tribo) of electrostatically chargeable powders, especially of toners for two-component developer is determined according to the following method. A toner/carrier mixture (developer) is activated in a glass bottle on a rolling fixture for a certain time. The developer is then placed into a measuring cell whose potential is zero. The toner is separated from the carrier by means of a selective pressure/vacuum and is removed by suction through a sieve or is blown off. This is the "hard" or "soft-blow-off" method.

The charge of the toner removed by suction or blown off is indicated as a voltage difference and calculated according to the following equation:

$$q/m = \frac{10\,U}{m}\ (\mu C/g),$$

in which m is the mass blown off (removed by suction). The toner is charged oppositely to the sign of the voltage difference.

Measuring conditions

Batch:
2% toner
98% carrier (spherical ferrite, 80–100 μm)
Activation:
Rolling fixture, 360 rpms in 40 ml glass bottle
Weighed portion 40 g developer

Multiple Activation

A specimen is activated several times in succession in this case This test comes closer to conditions in practice since the developer is charged in more or less regular intervals in a copier.

Charge Retention Time

In this case, the specimen was activated 30 minutes and measure according to the times indicated in the graph. The result shows how stable a charge once applied is retained for a rather long period of time.

The following formulation was used:
Raw toner
 93% toner resin OT 5201
 7% pigment black Printex 150 T
Coated toner 0.3% Areosil according to Examples 1, 2, 3 and was added in each instance to the raw toner Silica AEROSIL R 972 is state of the art according to U.S. Pat. No. 3,720,617.

Multiple Activation

In contrast to the raw toner, all coated toners exhibit a distinctly more stable charge level. When coated with silica 1 or 2, the final value is no longer significantly influenced even after a single activation. The charge stability is improved in comparison to the raw toner by means of using silica 3; however, the q/m value rises continuously in the course of the measuring series. The toner coated with silica 4 exhibits a stable charge level after the second activation The results of this measurement are shown in FIG. 1. Charge retention time The raw toner does retain the once-applied charge (activation time for all types 30 min.) in a stable manner even after 24 hours but falls far short of the final value found in multiple activation. In distinction to the raw toner, the coated toners have the advantage that as the standing time increases, the charges reach the particular final value found in the multiple activation test. This advantage be comes apparent in practice in the following manner: The electrostatic charge retains the level of the values found in the multiple activation even after very long standing times of the toner, regardless of the prior history of the toner. The toner coated with silicas 1 and is also the most stable during the charge retention time. The result of this measurement are shown in FIG. 2.

In sum, the following advantages result from the use of the silicas of the invention:

The charge stability of commercially available two-component dry toners is distinctly improved under the conditions of usage described herein, The maximum electrostatic charge achieved in multiple activation is reached and retained even after rather long storage times and standstill times of copiers, The toners coated with the silicas of the invention exhibit low activation energy (activation energy=-energy which is required order to achieve maximum q/m value), The flowability of commercially available two-component dry toners is distinctly improved by means of the coating with silicas 1–4.

Comparison with the state of the art according to U.S. Pat. No. 3,720,617.

U.S. Pat. No. 3,720,617 describes the use of the silica Aerosil R 972 in powder toners. Aerosil R 972 is cited in FIGS. 1 and 2 in addition to the raw toner and the silicas of the invention.

It is clear that, in a comparison of the silicas of the invention with Aerosil R 972, that Aerosil R 972 brings about a considerably higher electrostatic charge.

In addition to so-called primary and secondary resins, a commercially available toner formulation consists of pigment black and a charge control substance in the resin matrix. The charge level is primarily determined by the toner resin and the charge control substance The charge properties such as charge stability, charge retention, activation energy and the powder properties are determined and optimized by the silica.

The silicas of the invention are an improvement of the art since they less strongly or hardly influence the charge level of the raw toner and have a very positive influence on the charge stability, activation energy and charge retention. This is also advantageous because separations of a greater or lesser degree constantly occur in the copier, which causes the concentration of the silica to be subject to certain variations in a long-time test. The use of the silicas of the invention renders these variations less of a problem since the influence on the charge level is less.

The silicon dioxides prepared in accordance with the invention and reacted with flour-containing silanes are negatively charged when they come in contact with magnetic powder such as e.g. iron powder or iron oxide powder or are mixed with each other. This feature renders the silicon dioxides of the invention especially suitable not only for improving the flowability but also as charge generator for the negative charge of the toner particles. The silicas of the invention can be used in an amount of 0.1 to 5% by weight relative to the amount of toner.

The silicon dioxides of the invention can either be added as free-flowing powder to the developer particles, clinging to the surface of the developer particles as described in the journal POWDER Technologie 59 (1989), pp. 45 to 52, or they are added into the matrix of the toner particles when the latter are melted for homogenization and subsequently ground.

The toner particles which can be mixed with the silicas of the invention are themselves known (see European Patent Application EP-A 0 293 009 and U.S. Pat. No. 3,720,617).

Production of the Toner 90 parts ATLAC T 500 (trade name of the Atlas Chemical Industries Corporation, Wilmington, Del. consisting of propoxylated bisphenol-A-fumarate polyester with a glass transition temperature of 51° C., a melting point in a range of 65° to 85° C., an acid value of 13.9 and a viscosity of 0.175, measured at 25° C. in a mixture of phenol orthodichlorobenzene (weight ratio 60/40), and 10 parts of Cabot Regal 400 (trade name of the Cabot Corporation, USA) black are placed into a kneader and heated to 120° C. until a melt forms. The kneading is then started. After approximately 30 minutes, the kneading was stopped and the mixture cooled down to room temperature (20° C.).

The mixture was thoroughly broken and ground at this temperature until a powder was produced which was further reduced with an air jet mill. Furthermore, an air classification was carried out for which combination of the apparatuses AFG (Alpine fluid bed counter-jet mill type 100, as mill, equipped with an ATP (Alpine Turboplex air classifier type 500 GS), as air classifier, were used. A further air classifying was achieved by using the Alpine multiplex laboratory zigzag classifier. The particle size distribution of the toner to be obtained was determined with known means such as e.g. a Coulter counter The average particle size diameter was 5 $\mu$m. The toner particles obtained were introduced into a mixing apparatus and mixed with the silicon dioxides of the invention. At the same time, known hydrophobed silicas were mixed in, in separate specimens, in order to produce reference specimens. In particular, the following silicas were used:

| Example No. | Hydrophobing agent | BET surface |
|---|---|---|
| Ex. 1 (reference) | $\gamma$-aminopropyl-Si trimethyl-Si | 150 m$^2$/g |
| Ex. 2 (reference) | dimethyl-Si | 110 m$^2$/g |
| Ex. 3 (reference) | trimethyl-Si | 200 m$^2$/g |
| Ex. 4 (according to the invention) | C$_4$F$_9$(CH$_2$)$_2$Si | 180 m$^2$/g |

The silicas were mixed in the following manner with the toner particles:

100 g toner and 105 g silicon dioxide additives were placed into a Janke and Kundel laboratory mill type IKA M 20 with a speed of 20,000 rpms. A uniform temperature of 20° C. was maintained thereby The mixing time was 15 seconds.

The flowability of the toner was distinctly improved by the addition of the silicas. The mixture obtained and consisting of toner hydrophobed silicon dioxide is further used for the production of and developer mixture for a two-component electrostatic process. After the addition of this toner—silicon dioxide mixture to a customary zinc nickel ferrite carrier mixture (almost 100 μm in size) in a ratio of 5% by weight relative to the carrier, the developer was activated by rolling it in a metal container with a diameter of 6 cm. The speed was 300 rpms for a period of 30 minutes. The degree of admission of the roller was 30%.

The developer mixture produced in this manner was examined further. The triboelectric charge of the toner was determined by a known blow-off method. The results are expressed in the ratio of charge to q/M. The exact description of this method is described in European patent application No. 89 200 766.7.

The experimentally measured results of the determination of the triboelectric charge yield the following information:

| Example | Triboelectric charge |
|---------|----------------------|
| 1 | $-1$ μC/g |
| 2 | $-14$ μC/g |
| 3 | $-13$ μC/g |
| 4 | $-18$ μC/g. |

Example 5 and 6

A colorless toner is produced in a manner similar to that described above. The sole exception was that no black was used.

The hydrophobed silicas of Examples 3 and 4 were added in an amount of 2.5 g to 100 g colorless toner. The developers were produced by the addition of the toner additive mixture to the carrier, such as described in Examples 1 to 4. The amount was 4% by weight. No useable developer could have been obtained if the silica according to Example 3 had been added. The ratio of charge to mass was too low and a dusty mixture displays separation phenomena.

In contrast to the above, the developer which comprised the silica coated in accordance with the invention according to Example displays a triboelectric value of—17 μC/g and yielded good results when used as electrophotographic developer.

What is claimed is:

1. A method of producing a surface-modified, pyrogenically produced silicon dioxide which has been surface modified with a composition consisting essentially of a chemical compound selected from the group consisting of:

$CHF_2-CH_2-O-(CH_2)_3Si(OCH_3)_3$, $CF_3-CHF-CF_2-O-(CH_2)_3-Si(OCH_3)_3$, $C_4F_9-CH_2-Si_2-(OCH_3)_3$ and $C_6F_{13}-CH_2CH_2-Si(OCH_3)_3$;

the modified silicon dioxide having the following characteristics:

| Appearance | loose white powder |
|---|---|
| Surface according to | 170 ± 30 |
| DIN 66 131 BET m²/g | |
| Average size of the primary particles nm | 12 |
| Stamping density according to DIN ISO 787/XI, JIS K 5101/18 g/l | 60 ± 20 |
| Drying loss according to DIN ISO 787/II, ASTM D 280, JIS K 5101/21 2 h at 105° C. in % by weight | <2, |
| pH according to DIN ISO 787/IX, ASTM D 1208, JIS K 5101/24 (in 4% aqueous dispersion) | 3.5–5.5; | the modified silicon dioxide having the following characteristics when said chemical compound is $CHF_2-CH_2-O-(CH_2)_3Si(OCH_3)_3$:

| Annealing loss according to DIN 55 921 relative to the substance dried 2 hours at 105° C. in % by weight | 6.5 ± 2.0 |
|---|---|
| Carbon content in % by weight | 2.4 ± 0.5; | the modified silicon dioxide having the following characteristics when said chemical compound is $CF_3-CHF-CF_2-O-(CH_2)_3-Si(OCH_3)_3$:

| Annealing loss according to DIN 55 921 relative to the substance dried 2 hours at 105° C. in % by weight | 7.0 ± 2.0 |
|---|---|
| Carbon content in % by weight | 2.2 ± 0.5; | the modified silicon dioxide having the following characteristics when said chemical compound is $C_4F_9-CH_2-CH_2-Si(OCH_3)_3$:

| Annealing loss according to DIN 55 921 relative to the substance dried 2 hours at 105° C. in % by weight | 7.5 ± 2.0 |
|---|---|
| Carbon content in % by weight | 2.2 ± 0.5; | the modified silicon dioxide having the following characteristics when said chemical compound is $C_6F_{13}-CH_2-CH_2-Si(OCH_3)_3$:

| Annealing loss according to DIN 55 921 relative to the substance dried 2 hours at 105° C. in % by weight | 8.5 ± 2.0 |
|---|---|
| Carbon content in % by weight | 2.0 ± 0.5; | said method comprising spraying a pyrogenically produced silica which has the following characteristics:

| Surface according to BET m²/g | 200 ± 25 |
|---|---|
| Average size of the primary particles nanometer | 12 |
| Stamping density according to DIN 53 194 g/l | approx. 50 |
| Drying loss according to DIN 55 921 (2 h at 105°) in % by weight | <1.5 |
| Annealing loss according to DIN 55 921 relative to substance dried 2 hours at 105° C. | <1 |

| | |
|---|---|
| (2 h at 100° C.) in % by weight | |
| pH according to DIN 53 200 | 3.6–4.3 |
| (in 4% aqueous dispersion) | |
| $SiO_2$ % by weight | >99.8 |
| $Al_2O_3$ % by weight | <0.05 |
| $Fe_2O_3$ % by weight | <0.003 |
| $TiO_2$ % by weight | <0.03 |
| HCl % by weight | <0.025 |
| Sieve residue according to DIN 53 580 according to Mocker (45/m) % | <0.05; | the proportions of $SiO_2$, $Al_2O$, $Fe_2O_3$, $TiO_2$ and HCl being determined on the substance which has been dried for 2 hours at 105° C., and the HCl content being a component of the annealing loss, with a composition consisting essentially of a chemical compound selected from the group consisting of the silanes:

$CHF_2-CH_2-O-(CH_2)_3-Si(OCH_3)_3$, $CF_3-CHF-CF_2-O-(CH_2)_3-Si(OCH_3)_3$, $C_4F_9-CH_2-CH_2-Si(OCH_3)_3$ and $C_6F_3-CH_2-CH_2-Si(OCH_3)_3$, intensively mixing the silica and said composition, and tempering the resulting mixture for a period of 1.5 to 2.5 hours at a temperature of 100° to 140° C.

* * * * *